United States Patent [19]

Rossmo

[11] Patent Number: 4,557,005
[45] Date of Patent: Dec. 10, 1985

[54] LEAF CUTTER BEE LARVAE EXTRACTING DEVICE

[76] Inventor: William Rossmo, 158 Mount Allison Crescent, Saskatoon, Saskatchewan, Canada, S7H 4A5

[21] Appl. No.: 636,870

[22] Filed: Aug. 2, 1984

[51] Int. Cl.$^4$ ............................................. A01K 51/00
[52] U.S. Cl. ...................................... 6/12 R; 6/12 A
[58] Field of Search .................... 6/12 R, 12 A, 12 M

[56] References Cited

U.S. PATENT DOCUMENTS

| | | | |
|---|---|---|---|
| 3,581,324 | 6/1971 | Davidson, Jr. | 6/12 A |
| 3,609,780 | 10/1971 | Cowen | 6/12 A |
| 3,965,509 | 6/1976 | Barber | 6/12 A |
| 4,234,986 | 11/1980 | Cox et al. | 6/12 R |

*Primary Examiner*—Robert P. Swiatek
*Attorney, Agent, or Firm*—Stanley G. Ade

[57] ABSTRACT

A hive section of plastic or wood moves along an upper raceway with the board immediately following the inner board, being supported on the underside by a support which is shaped to follow the contour of the cross section of the board for maximum support. A transverse impact bar extends between a pair of spaced and parallel endless chain and sprocket assembly and is moved thereby to strike the upper side of the innermost board thus shearing it away from the hive section and moving it downwardly between a set of guides. The impact bar is shaped to engage substantially the entire upper surface of the board. The impact bar moves the board between a pair of comb assemblies on the lower ends of the guide bars which clears out the cocoons and leaves them to fall into a catch pan or stacked upright whereupon flippers moves them away and into the catch pan so that they are not struck by the next following board. The cleared board is moved downwardly and then forwardly onto a lower raceway so that when the entire hive section has been cleaned, it is in a reassembled stacked position on the lower raceway ready for reuse.

14 Claims, 10 Drawing Figures

4,557,005

LEAF CUTTER BEE LARVAE EXTRACTING DEVICE

BACKGROUND OF THE INVENTION

This invention relates to new and useful improvements for the removal of larvae in cocoon form from between individual boards forming a hive section. Conventionally, such work has been expensive and unpleasant particularly when the frames are designed for a specific bee specie such as the leaf cutter bees comprise individual boards having spaced and parallel crests and slots on either side thereof which, when stacked, define longitudinal extending substantially cylindrical bores therebetween into which the leaf cutter bees deposit their larvae in cocoon form.

Attempts have been made in the past to clean such boards mechanically, the closet art known to applicant being U.S. Pat. No. 3,965,509. However in this particular patent, the boards are forced past projecting pins in order to clean the larvae from the grooves and adjustability is difficult in order to ensure that the grooves are cleaned but at the same time preventing damage according to the boards, particularly when same are manufactured from styrofoam rather than wood.

The present invention overcomes difficulties inherent with hand cleaning and devices such as that shown in the above identified U.S. Patent and one aspect of the invention is to provide apparatus for cleaning and removing cocoons from the slots of hive frames of the type formed by a plurality of boards stacked together to define a plurality of spaced and parallel elongated substantially cylindrical bores; comprising in combination a supporting framework, a source of power in said framework, an upper input raceway supported in said framework, a board shearing and slot cleaning assembly in said framework at the inner end of said upper raceway, means in said assembly adjacent the inner ends of said upper raceway for supporting the underside of the board immediately adjacent the innermost board of said hive section on said upper raceway, means in said assembly for engaging the upper side of the innermost board of said hive section, separating same from said hive section in shearing motion and moving said innermost board downwardly, guide means in said assembly guiding said innermost board downwardly, a front comb mounted on the lower ends of said guide means and extending across said assembly, a mating further comb assembly mounted in said framework and extending across said framework, said innermost board being engaged by said comb assemblies one on each side thereof, whereby cocoons in slots are retained as said board moves past said comb assemblies, means to remove said cocoons from adjacent said comb assemblies, a lower raceway to receive said cleaned boards, and means to move said board from below said comb assemblies to said lower raceway.

With the foregoing in view, and other advantages as will become apparent to those skilled in the art to which this invention relates as this specification proceeds, the invention is herein described by reference to the accompanying drawings forming a part hereof, which includes a description of the preferred typical embodiment of the principles of the present invention, in which:

DESCRIPTION OF THE DRAWINGS

In the drawings like characters of reference indicate corresponding parts in the different figures.

DETAILED DESCRIPTION

Figure 1:
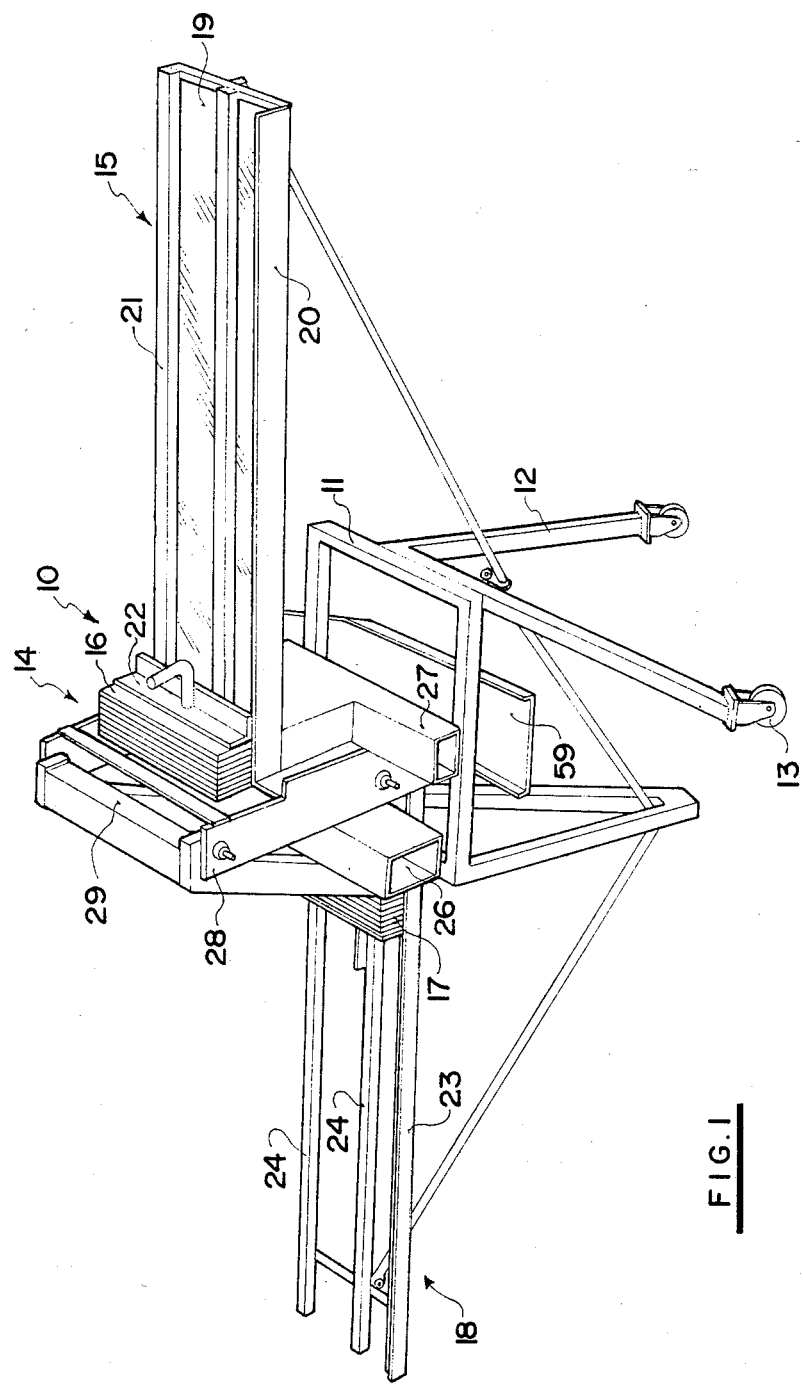
FIG. 1 is a partially schematic isometric view of the apparatus.

Proceeding therefore to describe the invention in detail, reference should first be made to FIG. 1 which shows the device collectively designated 10 supported upon a substantially rectangular frame 11 and including three downwardly extending legs 12 having castors 13, said legs being positioned so that the entire assembly is situated at an angle to the longitudinal axis thereof both for comfort of operation and to facilitate the movement of a hive section into and out of the machine as will hereinafter be described.

The rectangular or supporting framework 11 supports the main element of the assembly, namely, a board shearing and slot cleaning assembly collectively designated 14.

An upper input raceway collectively designated 15 allows a hive section 16 to be fed into the machine with the individual boards 17 (see FIG. 6) being restacked in a lower or outlet raceway assembly collectively designated 18.

The input or upper raceway 15 includes the planar base 19 which is also sloped relative to the longitudinal axis of the machine, and having a lower side member 20 and an upper side member 21 either one of which or both may be adjustable within limits to suit hive sections which may be slightly misaligned, or slightly larger or smaller than standard.

A manual pusher assembly 22 slides within the upper raceway 15 and assists in moving the hive section 16 into feeding position of the assembly 14 as will hereinafter be described.

The lower raceway 18, which extends upon the opposite side of the assembly 14 to the upper raceway 15 and at a lower level thereof, also consists of a lower rail or side member 23. This lower member is in the form of an angle iron and spaced and parallel support members 24 assist in supporting the individual boards 17 after they have been through the machine and have been cleaned and separated from the hive section 16.

Figure 2:
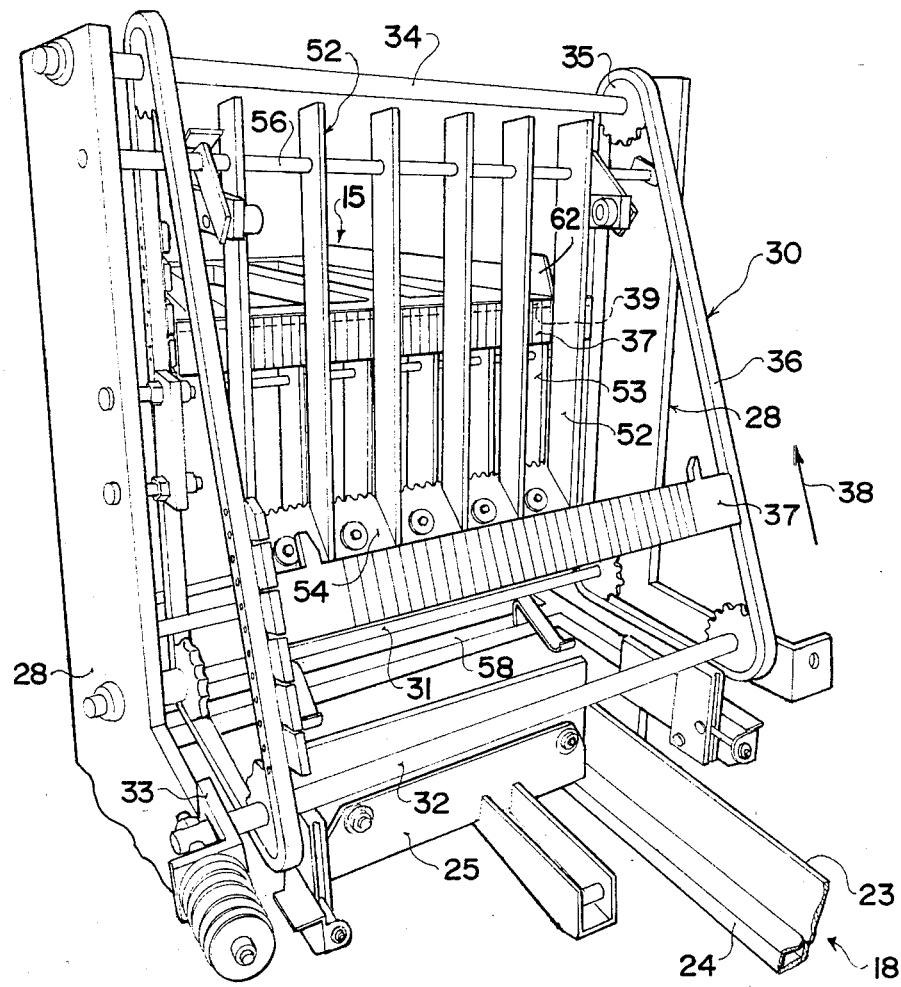
FIG. 2 is a partially schematic rear elevation of the main assembly.

Reference to FIG. 2 will show a lower pusher element or member 25 running or mounted upon the lower raceway and held frictionally in order to prevent the individual board 17 from toppling.

The assembly 14 includes a transversely extending chute 26 supported within the framework 11 with a further transverse chute 27 also supported within the framework 11 but situated rearwardly and below the main chute 26.

A pair of side plates 28 extend upwardly from the frame 11 in spaced and parallel relationship and an upper transverse member 29 maintains these side plates 28, in position.

The side plates 28 support, among other things, a pair of spaced and parallel chain and sprocket assemblies collectively designated 30, one upon each side of the assembly as clearly shown in FIG. 2. The sprocket and chain assemblies 30 include a main drive shaft 31 extending between adjacent the bases of the side plates 28, a lower idler shaft 32 journalled for rotation within rearwardly extending extensions 33 from adjacent the bases of the side plates 28 and an upper idler shaft 34 journalled for rotation and extending between adjacent the upper ends of the side plates 28. Sprocket wheels 35 are secured to each end of the drive shaft 31 and the idler shafts 32 and 34 and endless sprocket chains 36 extend around the two sets of sprocket wheels as clearly shown in FIG. 2.

Figure 7:
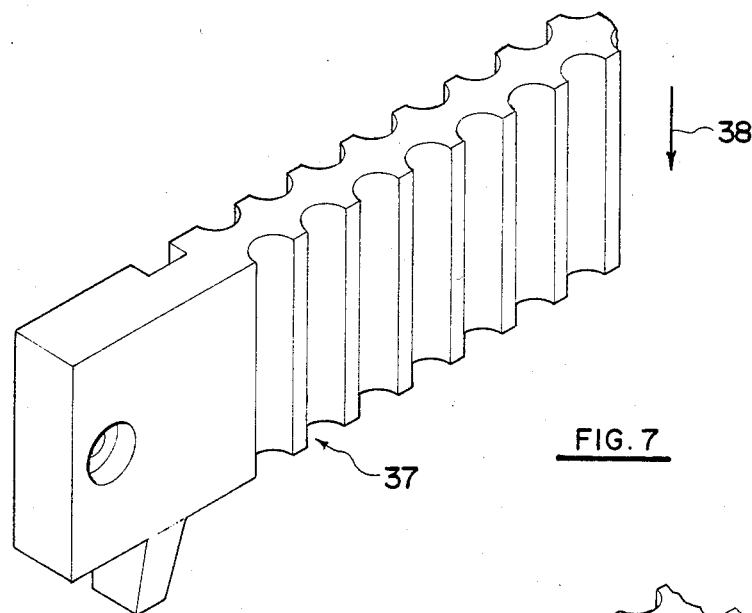
FIG. 7 is a fragmentary isometric view of the impact bar.

An impact bar 37 is secured to the chains 36 and extends transversely therebetween and the configuration of this impact bar 37 is clearly shown in FIG. 7.

Figure 8:
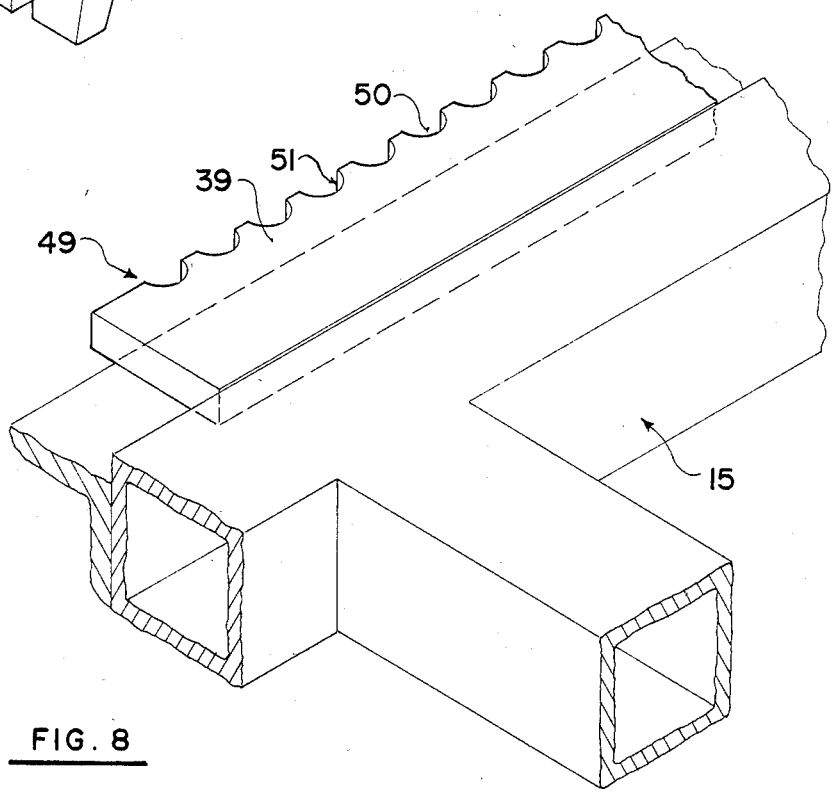
FIG. 8 is a partially schematic fragmentary view of the striker bar or support bar.

A source of power (not illustrated) in the form of an electric motor is operatively connected to drive shaft 31 and rotates the sprocket chains 36 in the direction of arrow 38 (FIG. 2). A striker plate 39 (see FIG. 8) is situated at the inner end of the upper raceway 15 and is contoured as illustrated in FIG. 8, the purpose of which will hereinafter be described.

Figure 5:
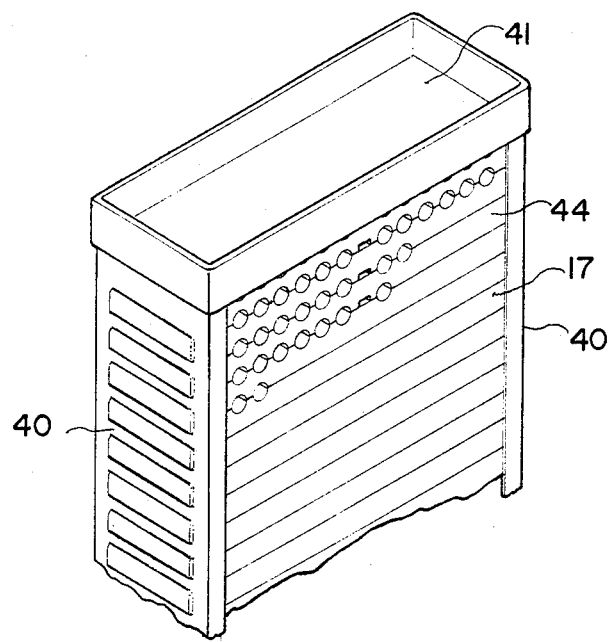
FIG. 5 is a partially schematic fragmentary isometric view of a hive section.

FIG. 5 shows a portion of a conventional hive section consisting of a plurality of substantially rectangular hive boards 17 stacked one on top of the other and held within side plates 40 and retained by end caps 41.

Figure 6:
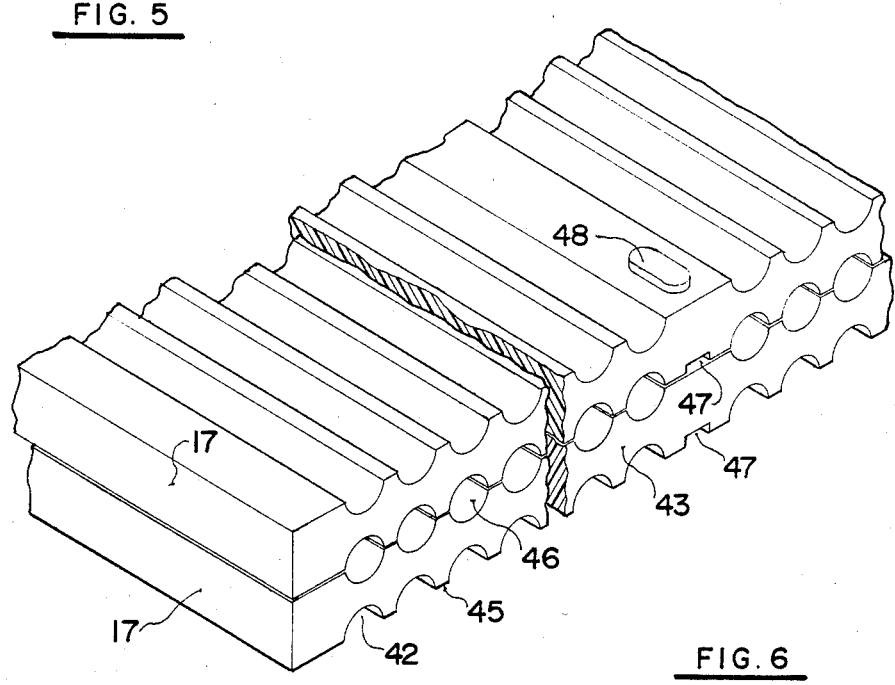
FIG. 6 is a fragmentary isometric view of two of the boards in interfacial relationship.

FIG. 6 shows a pair of these hive boards in interfacial relationship and it will be noted that each board consists of a plurality of substantially semi-circular grooves 42 extending from one longitudinal edge 43 towards the other 44, said spaced and parallel semi-circular grooves 42 being separated by spaced and parallel crests 45. The individual grooves 42 on each side of the board 17 are opposite one another as are the crests 45 so that when the boards are aligned in interfacial relationship as shown in FIG. 6, the grooves and crests define transversely extending substantially cylindrical bores 46. Centrally of the boards 17, a location groove 47 may be provided on one side of each board with locating keys 48 on the other side so that when they are stacked, the matching grooves 42 align with one another to define the aforementioned bores 46.

The hive section, as hereinbefore mentioned, is adapted to receive leaf cutter bees who lay their larvae encased within a cocoon, in the longitudinal bores and when the sides 40 and the end plates 41 are removed from the hive section, these cocoons tend to hold the boards together in a block and the individual boards have to be separated from one another so that the cocoons containing the larvae can be removed for hatching purposes.

The hive section removed from the casing is placed upon the upper input raceway 15 and the pusher 22 is used to move the block of adhered boards towards the inner end of the raceway.

Figure 9:
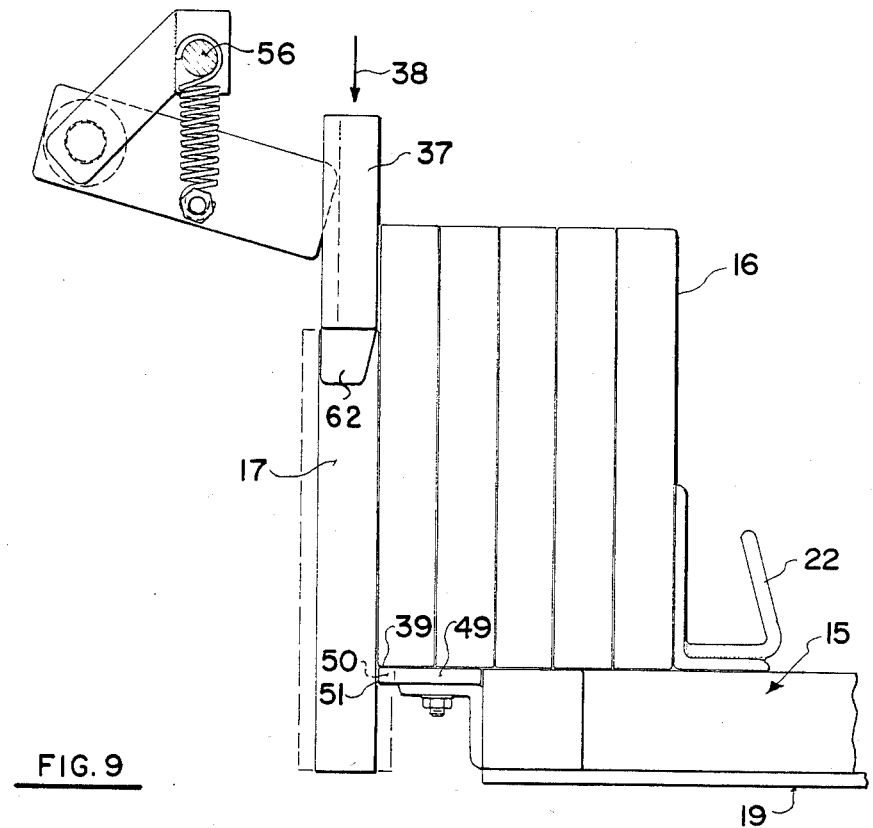
FIG. 9 is a fragmentary isometric view of the impact bar, striker bar and the boards.

The striker plate 39 is contoured so that the inner surface 49 is provided with a plurality of semi-circular grooves 50 separated by ridges 51, the contour of which follows the contour of one side of the board 17. This is spaced from a plurality of front spaced and parallel vertical guides 52 so that when the innermost board of the block 16 registers against the front guides 52, the striker plate 39 supports the front side of the board next to the innermost board (see FIG. 9).

The impact bar carried by the sprocket chains 36, is shaped as shown in FIG. 7 with a configuration similar to the cross sectional configuration of one of the boards so that when it moves downwardly on the front run of the chains, it engages the upper edge of the innermost board and shears it from the next succeeding board and moves it downwardly together with the cocoons adhered within the grooves, towards comb assemblies maintained vertically by means of the aforementioned front guides 52 and corresponding rear guides 53 which extend below the striker bar 39. The comb assembly includes the front comb assembly 54 flexibly supported upon the lower ends of the front guides 52 and a rear comb assembly 55 adjustably supported between the lower ends of the rear guides 53 and the framework 11. The front guides are pivotally supported upon a cross shaft 56, by the upper ends thereof, said cross shaft extending between adjacent the upper ends of the side plates 28 just below shaft 34 and the front combs 54 are mounted so that if the individual boards are slightly misaligned or vary in thicknesses, the comb can move to follow the contours of the grooves.

Figure 3:
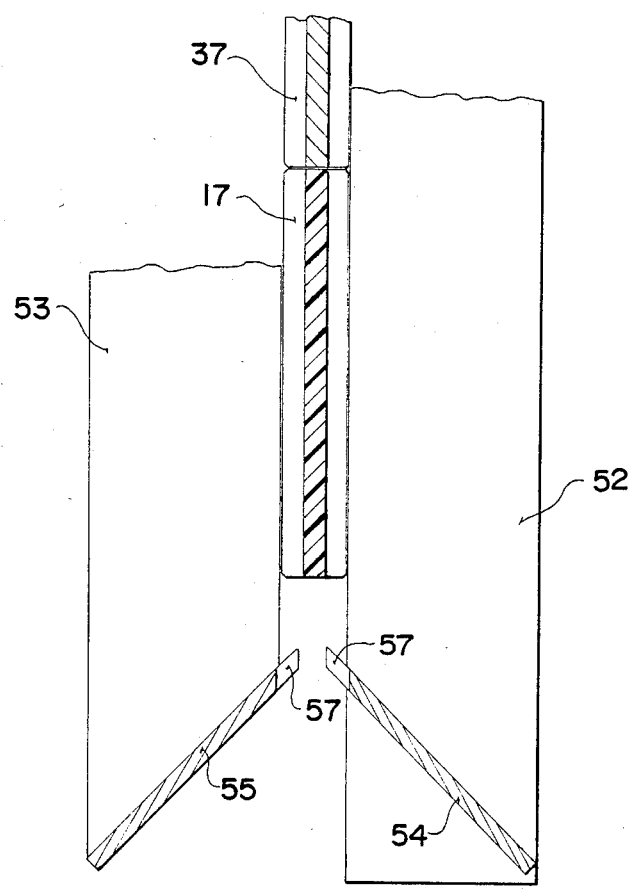
FIG. 3 is a partially schematic fragmentary side view of the comb assemblies.
Figure 4:
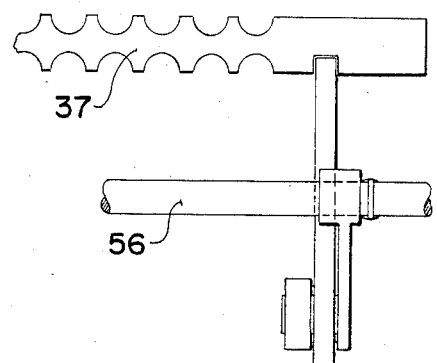
FIG. 4 is a fragmentary section of one chain showing the board adjusting device.

Each comb consists of a plurality of semi-circular apertures in the upper edge thereof defining crests, the configuration of which is similar to the grooves in the board passing therebetween and it will be noted that these combs incline upwardly towards one another as clearly shown in FIGS. 2 and 3.

The board is moved downwardly by the impact bar, between the front and rear guides until the lower edge thereof meets the teeth 57 of the two combs and these teeth clean out the cocoons containing the larvae, on both sides of the board simultaneously whereupon the board passes through the teeth to the area below the drive shaft 31. They engage the inner end of the lower raceway 18 and the impact bar moves from the upper surface thereof and returns upwardly in the direction of arrow 38 as shown in FIG. 2 ready to separate the next succeeding board which is now registering against the front edges of the front guides 52 urged by the manual pusher 58 which is located at the inner end of the raceway and is timed to move the board just cleaned, to the inner end of the raceway against the friction pusher 25.

The cocoons cleaned from the grooves fall into a discharge or collection chute 59 extending under the machine and sloping downwardly towards the lower side as clearly shown in FIG. 1. Sometimes these cocoons remain stacked one upon the other on the teeth 57 of the comb and have to be removed before the next board decends and crushes same and a set of resilient flippers 60 are mounted on shaft 61 and are actuated by the rotation of the sprocket and chain assemblies, to move across the upper edges of the combs after the board has cleared, in order to ensure that the cocoons are removed from the teeth before the next board enters the comb area.

Figure 10:
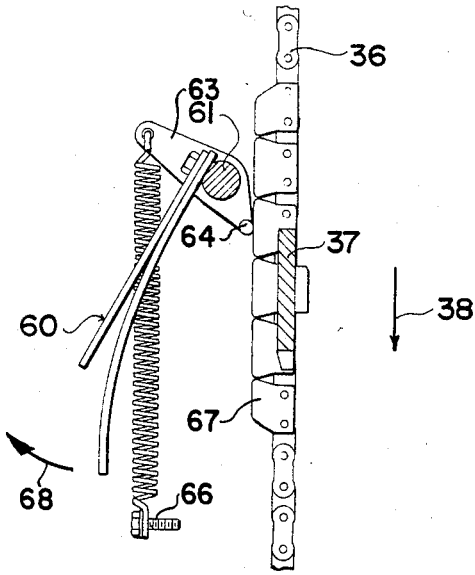
FIG. 10 is a fragmentary, isometric partially schematic view of the flipper assembly at the lower rear side of the comb assembly.

Reference to FIG. 10 will show these flippers on shaft 61, together with cam lever 63 having a cam follower 64 on one end thereof and a spring 65 extending between the other end and an anchor screw 66 engaged with a convenient frame member (not illustrated). The spring normally urges the follower 64 in contact with the outside of one of the chains 36. Adjacent each striker bar 37, where it is secured to chain 36, is a plurality of cams 64 which strike the follower thus moving the flippers in the direction of arrow 68 in order to remove any cocoons which may be stacked in the comb area.

The vertical guides 52 are spaced so that they are engaged by the portion of the board or crests 45 and they are centered by board alignment tabs 62 secured to each sprocket chain 36 and extending inwardly therefrom, in advance of the impact bar 37. These center the boards as they are sheared from the hive section and ensure that they are in accurate registration before entering the combs 55.

Advantages include the following:

1. The sloped raceways make it easy to unload and load and align broken hive sections as there is no jamming between the two sides as happens in horizontally located raceways.

2. The device is designed to handle poorly assembled hives. The input raceway can be tilted and the side guide can be adjusted to easily handle out of square hives thus assuring complete contact with the input throat and a square complete hit by the impact bar. The board alignment tabs 62 ensure that even offset boards in hives are aligned before impact.

The floating comb system allows treatment of boards that may be warped or have thickness variations. Not only will they handle boards that are uniformly thick or thin but the combs will flex to accept boards that are large on one end and smaller on the other. The combs keep in close and accurate registration for complete board cleaning and minimal cocoon stress yet do no actually touch the board surfaces.

4. The semi-circular configuration of the combs allows minimum clearance to the grooved surfaces of the board thereby cleaning out all chaff and cocoons, treating the cocoons gently and not damaging the boards.

The contoured striker plate 39 is used at the input throat and when operating on styrofoam boards, gives maximum underside support thereby preventing board damage as the impact bar shears off the boards yet prevents any damage to the cocoons which is often caused by a conventional uncontoured striker plate.

Although the device is designed primarily for use with styrofoam boards or boards made of a similar material, nevertheless it is readily adapted for use with conventional wooden boards, it being merely necessary to change a minimum number of components.

Since various modifications can be made in my invention as hereinabove described, and many apparently widely different embodiments of same made within the spirit and scope of the claims without departing from such spirit and scope, it is intended that all matter contained in the accompanying specification shall be interpreted as illustrative only and not in a limiting sense.

I claim:

1. Apparatus for cleaning and removing cocoons from the slots of hive frames of the type formed by a plurality of boards stacked together to define a plurality of spaced and parallel elongated substantially cylindrical bores; comprising in combination (a) supporting framework,
(b) a source of power in said framework,
(c) an upper input raceway supported in said framework,
(d) a board shearing and slot cleaning assembly in said framework at the inner end of said upper raceway,
(e) means in said assembly adjacent the inner ends of said upper raceway for supporting the underside of the board immediately adjacent the innermost board of said hive section on said upper raceway,
(f) means in said assembly for engaging the upper side of the innermost board of said hive section, separating same from said hive section in shearing motion and moving said innermost board downwardly,
(g) guides in said assembly pivotally mounted by the upper ends therefor, for guiding said innermost board downwardly,
(h) a front comb mounted on the lower ends of said guide means and extending across said assembly, and being movable with said guides whereby said comb aligns with the contour of said board, a mating further comb assembly mounted in said framework and extending across said framework, said innermost board being engaged by said comb assemblies one on each side thereof, whereby cocoons in said slots are retained as said board moves past said comb assemblies, said comb assemblies inclining upwardly and inwardly towards one another and having board surface engaging edges,
(i) means to remove said cocoons from adjacent said comb assemblies,
(j) means to move said board from below said comb assemblies to said lower raceway.

2. Apparatus according to claim 1 in which said upper raceway is inclined relative to the longitudinal axis thereof and includes adjustable sides thereon.

3. Apparatus according to claim 2 in which each of said boards includes a plurality of spaced and parallel crests and valleys on each side thereof extending from one longitudinal edge to the other, said crests on one side being opposite said crests on the other side, said valleys on one side being opposite said valleys on the other side.

4. Apparatus according to claim 1 in which said means for engaging the upper side of said innermost board of said hive section includes a pair of spaced apart endless sprocket and chain assemblies, an impact bar secured by the ends thereof, one to one chain and the other to the other chain of said sprocket and chain assemblies and extending transversely therebetween, said sprocket and chain assemblies being operatively connected to said source of power.

5. Apparatus according to claim 4 in which said impact bar has a configuration similar to the cross sectional configuration of one of said boards.

6. Apparatus according to claim 5 in which each of said boards includes a plurality of spaced and parallel crests and valleys on each side thereof extending from one longitudinal edge to the other, said crests on one side being opposite said crests on the other side, said valleys on one side being opposite said valleys on the other side.

7. Apparatus acccording to claim 6 in which said means to remove said cocoons from adjacent said comb assemblies includes a set of resilient flippers mounted transversely of said board shearing and slot cleaning assembly adjacent and substantially between said guide mans and means on said chains of said sprocket and chain assemblies to actuate said flippers after said cocoons are removed from said board, to move said cocoons away from the board next being cleaned.

8. Apparatus according to claim 5 in which said means to remove said cocoons from adjacent said comb assemblies includes a set of resilient flippers mounted transversely of said board shearing and slot cleaning assembly adjacent and substantially between said guide means and means on said chains of said sprocket and chain assemblies to actuate said flippers after said cocoons are removed from said board, to move said cocoons away from the board next being cleaned.

9. Apparatus according to claim 4 in which each of said boards includes a plurality of spaced and parallel crests and valleys on each side thereof extending from one longitudinal edge to the other, said crests on one side being opposite said crests on the other side, said valleys on one side being opposite said valleys on the other side.

10. Apparatus according to claim 9 in which said means to remove said cocoons from adjacent said comb assemblies includes a set of resilient flippers mounted transversely of said board shearing and slot cleaning assembly adjacent and substantially between said guide means and means on said chains of said sprocket and chain assemblies to actuate said flippers after said cocoons are removed from said board, to move said cocoons away from the board next being cleaned.

11. Apparatus according to claim 4 in which said means to remove said cocoons from adjacent said comb assemblies includes a set of resilient flippers mounted transversely of said board shearing and slot cleaning assembly adjacent and substantially between said guide means and means on said chains of said sprocket and chain assemblies to actuate said flippers after said cocoons are removed from said board, to move said cocoons away from the board next being cleaned.

12. Apparatus according to claim 4 in which said means to move said board from below said comb assemblies to said lower raceway includes a power operated pusher assembly actuated by said sprocket and chain assembly to move the cleaned board from a position immediately below said guide means, to the inner end of said lower raceway to move said board away from the board next being cleaned.

13. Apparatus according to claim 1 in which the configuration of said comb assemblies is similar to the cross sectional configuration of each side of one of said boards.

14. Apparatus according to claim 1 in which each of said boards includes a plurality of spaced and parallel crests and valleys on each side thereof extending from one longitudinal edge to the other, said crests on one side being opposite said crests on the other side, said valleys on one side being opposite said valleys on the other side.

* * * * *